(12) United States Patent
Toda

(10) Patent No.: US 6,513,000 B1
(45) Date of Patent: Jan. 28, 2003

(54) SIMULATION METHOD OF WIRING TEMPERATURE RISE

(75) Inventor: Takeshi Toda, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/281,066

(22) Filed: Mar. 10, 1999

(30) Foreign Application Priority Data

Mar. 11, 1998 (JP) .......................................... 10-060226

(51) Int. Cl.⁷ ........................... G06F 7/60; G06F 17/10; G06F 17/50; G01N 25/18; G01V 3/18
(52) U.S. Cl. .............................. 703/13; 703/2; 324/451; 324/543; 374/44; 374/57; 438/468
(58) Field of Search ............................ 703/2; 324/457; 438/468; 374/44

(56) References Cited

U.S. PATENT DOCUMENTS

| | | | |
|---|---|---|---|
| 3,474,530 A | * 10/1969 | Ainslie et al. | ............... 438/469 |
| 4,014,729 A | * 3/1977 | Dybwad | ..................... 228/107 |
| 4,483,629 A | * 11/1984 | Schwarz et al. | ............... 374/57 |
| 4,722,609 A | * 2/1988 | Epstein et al. | ................ 374/30 |
| 4,751,099 A | * 6/1988 | Niino et al. | ................ 437/450 |
| 5,264,377 A | * 11/1993 | Chesire et al. | ................ 438/11 |
| 5,291,142 A | * 3/1994 | Ohmi | ......................... 324/719 |
| 5,408,638 A | * 4/1995 | Sagawa et al. | ............... 716/20 |
| 5,497,076 A | * 3/1996 | Kuo et al. | ................ 324/158.1 |
| 6,038,383 A | * 3/2000 | Young et al. | ................... 716/5 |
| 6,054,868 A | * 4/2000 | Borden et al. | ............... 324/752 |

FOREIGN PATENT DOCUMENTS

| JP | 4-283863 | 10/1992 |
|---|---|---|
| JP | 5-233589 | 9/1993 |
| JP | 7-283283 | 10/1995 |

OTHER PUBLICATIONS

Katto et al.; "Wafer–level jramp andj–constant electromigration testing of conventional and sweat patterns assisted by a thermal & electrical simulator"; IEEE 1991 Reliability Physics Symp.; pp. 298–305; Apr. 1991.*

Harmon et al.; "Thermal conductance of IC interconnects embedded in dielectrics"; IEEE 1998 Integrated Reliability Workshop; pp. 1–9; Oct. 1998.*

Liew et al.; "Effects of high current pulses on integrated circuit metalization reliability"; IEEE–I–THERM '88; pp. 3–6; May 1988.*

Lloyd et al.; "Electromigration in copper conductors"; Thin Solid Films; pp. 135–141; Jun. 1995.*

Ito; "Dynamic analysis of pool–cooled superconductor and MPZ"; Cryogenics; pp. 159–162; Mar. 1996.*

(List continued on next page.)

Primary Examiner—Hugh M. Jones
(74) Attorney, Agent, or Firm—Sughrue Mion, PLLC

(57) ABSTRACT

A heat capacity $C_1$ is obtained by conducting two-dimensional thermal analysis simulation to the cross-section of a wiring. Next, based on one-dimensional approximate equation of $\theta_0=(Q_0/2)\,(\lambda\cdot SC1)^{-\frac{1}{2}}$ along a wiring length direction, a wiring temperature rise $\theta_0$ in the void is obtained. In the expression, $\theta_0$ is a rise in wiring temperature in the void, $Q_0$ is a thermal quantity of the void in the wiring, $\lambda$ is a heat conductivity of the wiring and S is a cross-sectional area of the wiring. The heat capacity $C_1$ may be obtained from an expression $C_1=\lambda'\{(w/t)+(2.80/1.15)(h/t)^{0.222}\}$. In the expression, W is wiring width, h is wiring thickness, t is substrate film thickness and $\lambda'$ is the heat conductivity of the substrate film. By so obtaining, it is possible to shorten analysis time, to save the capacity of a memory and that of a disk for use in calculation, to obtain a simpler analysis model and to facilitate creating a mesh.

1 Claim, 5 Drawing Sheets

OTHER PUBLICATIONS

Shih et al.; "Transmission electron microscopy of Al–Cu interconnects during in–situ electromigration testing"; Thin Solid Films; pp. 103–117; Jan. 1997.*

Hu; "Electromigration failure mechanisms in bamboo–grained Al(Cu) interconnections"; Thin Solid Films; pp. 124–134; May 1995.*

Gardner et al.; "Mechanical stress as a function of temperature in aluminum films"; IEEE Trans. Electron Devices; pp. 2160–2169; Dec. 1988.*

Shinzawa et al.; "Molecular dynamics simulation of Al grain boundary diffusion for electromigration failure analysis"; IEEE 1998 Int. Tech. Conf.; pp. 30–32; Jun. 1998.*

Yankee et al.; "Response of aged line/stud structures to stepped current stressing"; IEEE Int. Reliability Workshop; pp. 103–109; Oct. 1996.*

Hsu et al.; "VLSI circuit design with built–in reliability using simulation techniques"; Proc. IEEE 1990 Custom Integ. Cir. Conf.; pp. 19.3/1–19.3/4; May 1990.*

Hinode et al.; "Dependence of electromigration lifetime on the square of current density"; IEEE 31st Ann. Int. Proc. Reliability Physics Symp.; pp. 317–326; Mar. 1993.*

Li et al.; "Electromigration: the time bomb in deep–submicron ICs"; IEEE Spectrum; pp. 75–78; Sep. 1996.*

Petrescu et al.; "Numerical analysis of electromigration in thin film VLSI interconnections"; CAS'95 Proc.; pp. 327–330; Oct. 1995.*

Enver et al.; "Finite element numerical modeling of currents in VLSI interconnects"; Proc. 7th Int. VLSI Multilevel Interconn. Conf.; pp. 149–156; Jun. 1990.*

O'Sullivan et al.; "Electromigration simulations for small scale structures" IEE Coll. Advanced MOS Bi–Polar devices; pp. 8/1–8/7 1995.*

Niehof et al.; "An empirical model for early resistance changes due to electromigration"; Solid–Stae Electronics; pp. 1817–1827; Oct. 1995.*

D'Haeger et al.; A new technique to characterize the early stages of electromigration–induced resistance changes at low current densities; Microelectronics and Reliability; pp. 1695–1698; Nov. 1996.*

De Munari et al.; "Design of a test structure to evaluate electro–thermomigration in power ICs"; Microelectronics and Reliability; pp. 1875–1878; Nov. 1996.*

Petrescu et al.; "2D modeling of mechanical stress evolution and electromigration in confined aluminum interconnects"; Proc. Microelectronics; pp. 629–632; Sep. 1997.*

Oberg et al.; "Computer modeling of contact degradation by intermetallic growth"; Electrical Contacts; pp. 41–45; Oct. 1997.*

Oberg et al.; "Computer simulation of the influence of intermetallics on the stability of electrical contacts"; Electrical Contacts; pp. 137–141; Sep. 1996.*

Kusuyama et al.; "Experimental study of electromigration at bamboo grain boundaries with a new test structure using the single–crystal aluminum interconnection"; IEEE Trans. Semiconductor Manuf.; pp. 15–19; Feb. 1996.*

Liew et al.; "Circuit reliability simulator for interconnect, via and contact electromigration"; IEEE Trans. Elect. Dev.; pp. 2472–2479; Nov. 1992.*

Dion; "EXTRA–EM: extraction of temperature and resistance for acceleration of electromigration at wafer–level"; Reliability Physics Symp.; pp. 287–297; Apr. 1991.*

Trattles et al.; "Three dimensional finite element determination of current density and temperature distributions in pillar vias"; VLSI Multilevel Interconnection Conf.; pp. 343–345; Jun. 1991.*

O'Neill; "Finite–element determination of interconnect track overheating"; Electronic Lett.; pp. 1484–1485; Oct. 1989.*

Gui et al.; "Simulation of temperature cycling effects on electromigration behavior under pulsed current stress"; IEEE Trans. Elect. Dev.; pp. 380–386; Feb. 1998.*

Liew et al.; "Reliability simulator for interconnect and intermetallic contact electromigration"; Reliability Physics Symp.; pp. 111–118; Mar. 1990.*

Liew et al.; "Effects of self–heating on integrated circuit metallization lifetimes"; Elect. Dev. Meeting; pp. 323–326; Dec. 1989.*

Goel et al.; "Electromigration in the VLSI interconnect metallizations"; Circuits & Syst. Proc.; pp. 821–824; Aug. 1989.*

Hunter; "The implications of self–consistent current density design guidelines comphrehending electromigration and Joule heating for interconnect technology evolution"; Elect. Dev. Meeting; pp. 483–486; Dec. 1995.*

Tao et al.; "Modeling electromigration failures in TiN/Al–alloy/TiN interconnects and TiN thin films"; Reliability Physics Symp.; pp. 371–377; Apr. 1995.*

Su et al.; "Measurement and modeling of self–heating in SOI nMOSFETs"; Elect. Dev.; pp. 69–75; Jan. 1994.*

Choi et al.; "A Monte Carlo simulation environment for wear out in VLSI systems"; VLSI Design; pp. 249–254; Jan. 1991.*

Hajj et al.; "A system for electromigration analysis in VLSI metal patterns"; Custom Integrated Cir. Conf.; pp. 4.4/1–4.4/4; May 1991.*

Khanna et al.; "Analytical models for sizing of VLSI power/ground nets under electromigration, inductive and resistive constraints"; Cir. & Sys. Symp.; pp. 2272–2275; Jun. 1991.*

Sakurai et al.; "Simple formula for two– and three–dimensional capacitances"; IEEE Trans. Elect. Dev.; pp. 183–185; Feb. 1983.*

Extended Abstracts; The Japan Society of Applied Physics and Related Socities (The $40^{th}$ Spring Meeting, 1993) 733 by Hamashima et al.

T. Sakurai et al., "Simple Formulas for Two– and Three–Dimensional Capacitances", *IEEE Transactions on Electron Devices*, vol. ED–30, No. 2, Feb. 1983, pp. 183–185.

* cited by examiner

SIMULATION METHOD OF WIRING TEMPERATURE RISE

BACKGROUND OF THE INVENTION

1. Field of the Invention

The present invention relates to a method of simulating wiring temperature rise due to a void causing the fault of refined wirings in a large scale integrated circuit. The present invention particularly relates to/a method of simulating wiring temperature rise by conducting two-dimensional thermal analysis on a wiring cross-section.

2. Description of the Related Art

The wiring fault in a large scale integrated circuit (to be referred to as "LSI" hereinafter) is caused by a phenomenon called electro-migration (to be referred to as "EM" hereinafter). The EM phenomenon occurs when aluminum atoms which constitute an LSI wiring are expelled by electrons, aluminum atoms are locally missed to cause a void in wiring, the void generally grows to fluctuate the wiring, thereby resulting in a fault. In the practical LSI wiring, current continuously flows thanks to a barrier metal intended to protect the aluminum wiring. The barrier metal is higher in specific resistance than aluminum. Due to this, if it is recognized that an increase in wiring resistance exceeds a certain level, it is judged as a wiring fault.

The characteristics of the EM phenomenon is expressed by an empirical expression (to be referred to as "MTTF" hereinafter) as shown in equation (1) below for the average life of a wiring:

$$\text{MTTF} \propto J^{-n} \exp(E_a/k\theta) \tag{1}$$

In the equation (1), J is current density, $\theta$ is temperature, $E_a$ is activation energy, k is a Boltzmann's constant and n is a constant. As is seen from equation (1), the higher the current density J is or the higher the temperature $\theta$ is, the more EM phenomenon is accelerated. Taking this into consideration, in the actual LSI wiring, to determine the reliability of the wiring, an acceleration test for a wiring fault is conducted at high current density and high temperature for a certain period of time. Based on the test, it is determined how long the wiring is used at the current density and temperature in a state in which an ordinary LSI is being used, to thereby determine the reliability of the wiring.

The problem with the wiring reliability test is how to determine a test temperature. In other words, since resistivity is concentrated into a portion of a void, temperature rises in the neighborhood of the void due to the local generation of Joule heat. A multi-layer wiring has, in particular, a disadvantage in that the respective wiring layers differ in temperature rise from one another. Due to this, it is necessary to correct temperatures used as parameters for the reliability test.

It is, thus, difficult to measure temperature rise if a void occurs. Temperature rise in a void portion has been conventionally measured by means of three-dimensional thermal analysis simulation. Specifically, while a thermal quantity and a constraint state are given, temperature rise is measured using three-dimensional thermal analysis simulation by a finite element method (Extended Abstracts; The Japan Society of Applied Physics and Related Societies (The 40th Spring Meeting, 1993) 733 by Hamashima et al.).

FIG. 1 is a flow chart showing a conventional simulation method in a case where an oxide film is formed on a silicon substrate, an aluminum wiring is formed on the oxide film and a void appears in th e wiring. FIG. 2 is a typical view of a wiring configuration.

First, the three-dimensional wiring configuration is created as shown in FIG. 2 (in step S1).

Next, it is assumed that a void occurs in the wiring in the model and the heat quantity of the void is $Q_0$. While the value $Q_0$ is applied to the three-dimensional void in the model which has been previously created and necessary temperature constraint is given to the void, a three-dimensional thermal analysis simulation is conducted (in step S2).

A temperature rise distribution $\theta_0(x)$ is obtained in wiring length direction. As shown in FIG. 3, a graph of temperature rise versus wiring length direction is created (in step S3).

Thereafter, a rise $\theta_0(0)$ in the temperature of the void is read from the graph of FIG. 3 (in step S4).

This conventional temperature simulation method has, however, the following disadvantages. First, the three-dimensional thermal analysis simulation takes a lot of time for analysis and calculation.

Second, the calculation amount is enormous for three-dimensional thermal analysis simulation, with the result that the capacity of a memory and that of a hard disk become high.

Further, the three-dimensional thermal analysis simulation is complicated in the input of an analysis model configuration and it takes a lot of time to create a mesh.

SUMMARY OF THE INVENTION

It is, therefore, an object of the present invention to provide a wiring temperature rise simulation method capable of shortening analysis time, saving the capacity of a memory and that of a disk for use in calculation, with a simple analysis model to thereby facilitate creating a mesh.

A wiring temperature rise simulation method according to the first aspect of the present invention comprises the steps of obtaining a heat capacity $C_1$ by conducting a two-dimensional thermal analysis simulation to a cross-section of a wiring; and obtaining a temperature rise $\theta_0$ at a portion of the wiring in which a void occurs, based on one-dimensional approximate equation $\theta_0 = (Q_0/2) (\lambda^* SC_1)^{-1/2}$ along a wiring length direction, where $\theta_0$ (measured in ° K.) is a wiring temperature rise at the portion of the void, $Q_0$ (measured in W, i.e. Watts) is a heat quantity of the void in the wiring, $\lambda$ (measured in [W/(° K. m)]) is a heat conductivity of the wiring and S (measured in $m^2$, i.e. meters squared) is a cross-sectional area of the wiring.

A wiring temperature rise simulation method according to the second aspect of the present application comprises the steps of obtaining a heat capacity $C_1$ from an equation of $C_1 = \lambda' \{(W/t) + (2.80/1.15)(h/t)^{0.222}\}$, where W is a wiring width, h is a wiring thickness, t is a substrate film thickness and $\lambda'$ is a heat conductivity of the substrate file; and obtaining a wiring temperature rise $\theta_0$ based on one-dimensional approximate expression of $\theta_0 = (Q_0/2)(\lambda^* SC_1)^{-1/2}$ along a wiring length direction, where $\theta_0$ is a temperature rise at a portion of the wiring in which a void occurs, $Q_0$ is a heat quantity of the void in the wiring, $\lambda$ is a heat conductivity of the wiring and S is a cross-sectional area of the wiring.

According to the present invention, not the conventional three-dimensional thermal analysis simulation method but the two-dimensional thermal analysis simulation method is used. In the present method, after a heating capacity is obtained, temperature rise $\theta_0$ is obtained by the one-dimensional approximate expression in wiring length direction. It is, therefore, possible to make a model configuration simple and to thereby greatly shorten time for creating a mesh and time for analysis. It is also possible to reduce the capacity of a memory and that of a disk for use in analysis and calculation.

As stated above, according to the present invention, it is possible to estimate the temperature rise of a wiring in the vicinity of a void with the same accuracy as in the conventional three-dimensional simulation by using two-dimensional thermal analysis simulation and the one-dimensional approximate expression. Due to this, it is possible to simplify an analysis model, to greatly shorten calculation time required for analysis and to considerably save the capacity of a memory and that of a disk required for the analysis.

DESCRIPTION OF THE PREFERRED EMBODIMENTS

Figure 1:
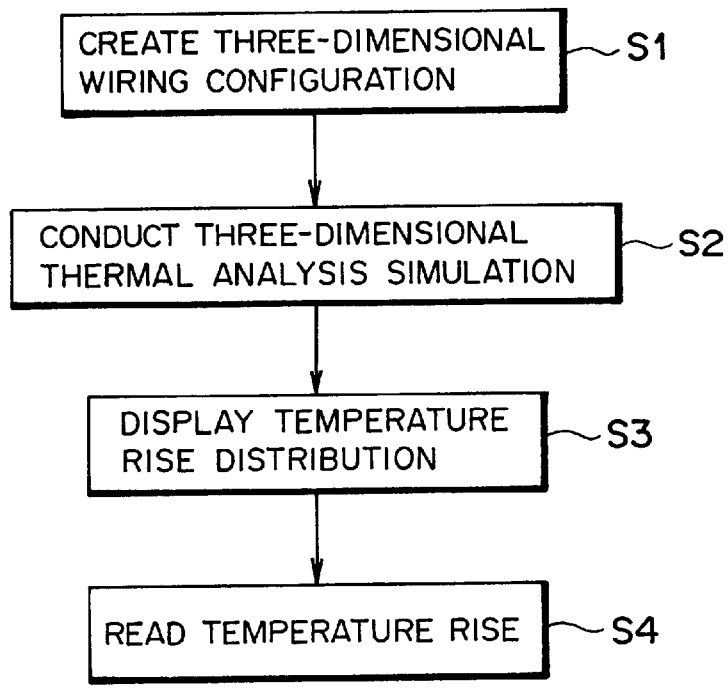
FIG. 1 is a flow chart showing a conventional method.
Figure 2:
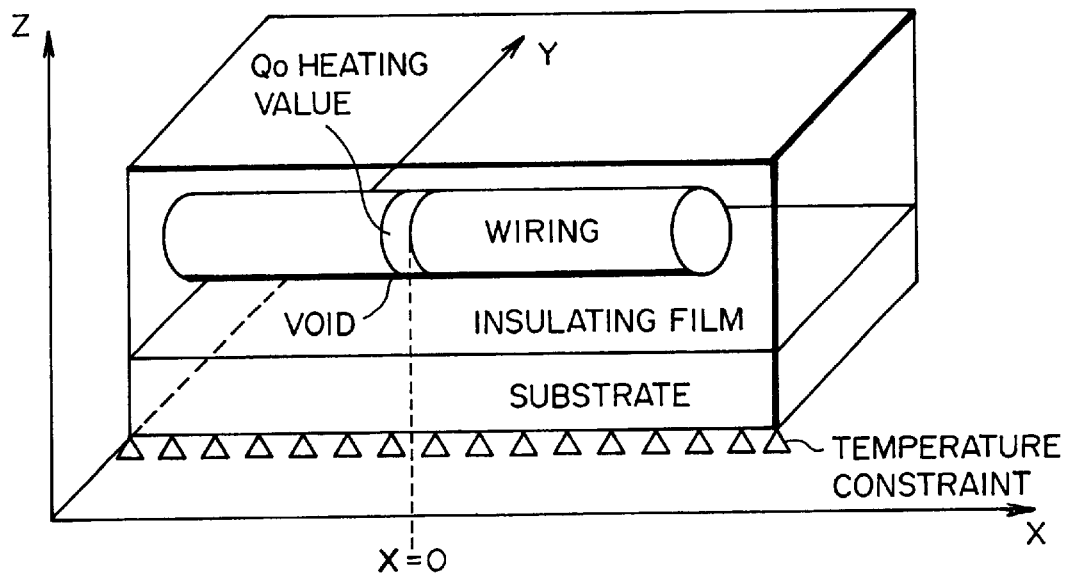
FIG. 2 shows a model of a conventional wiring configuration.
Figure 3:
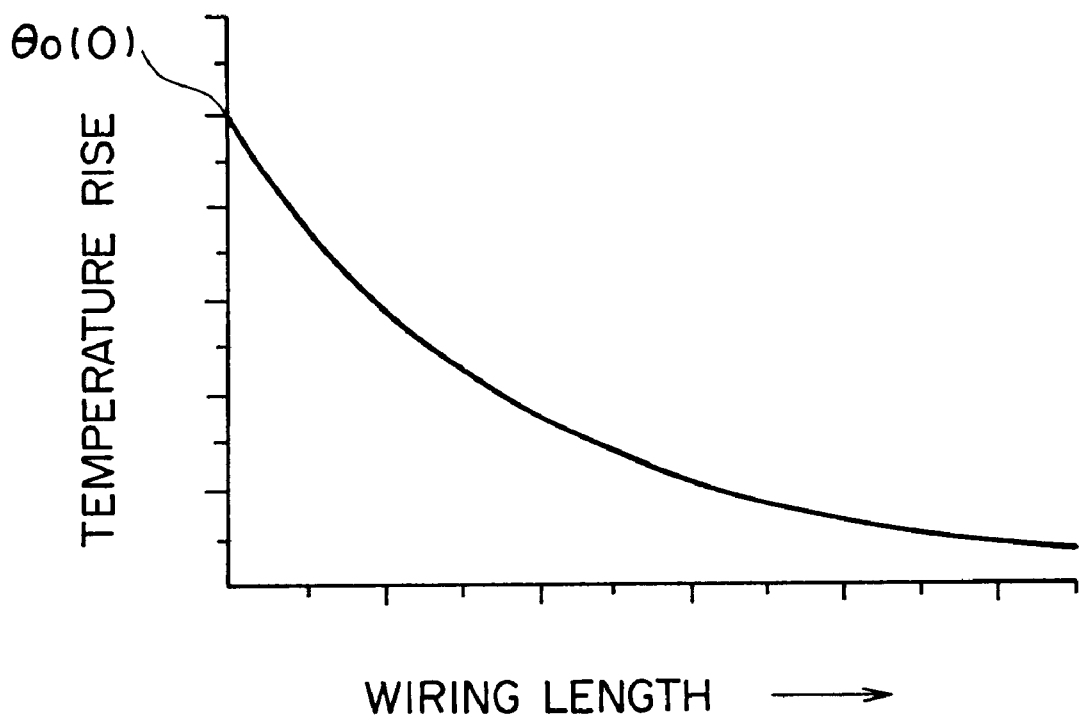
FIG. 3 is a graph showing temperature rise distribution obtained by the conventional method.
Figure 4:
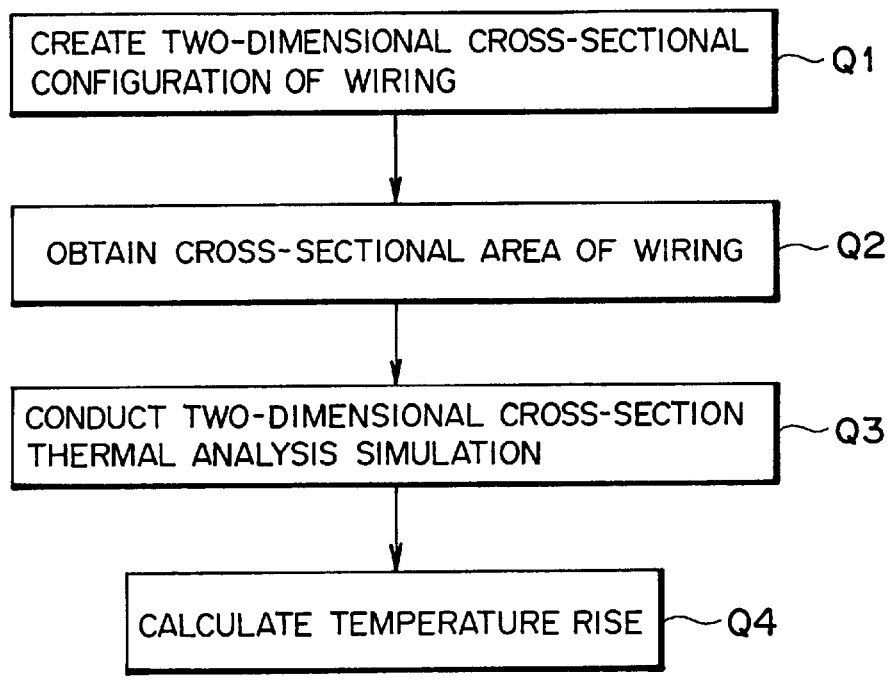
FIG. 4 is a flow chart showing a method in one embodiment method according to the present invention.
Figure 5:
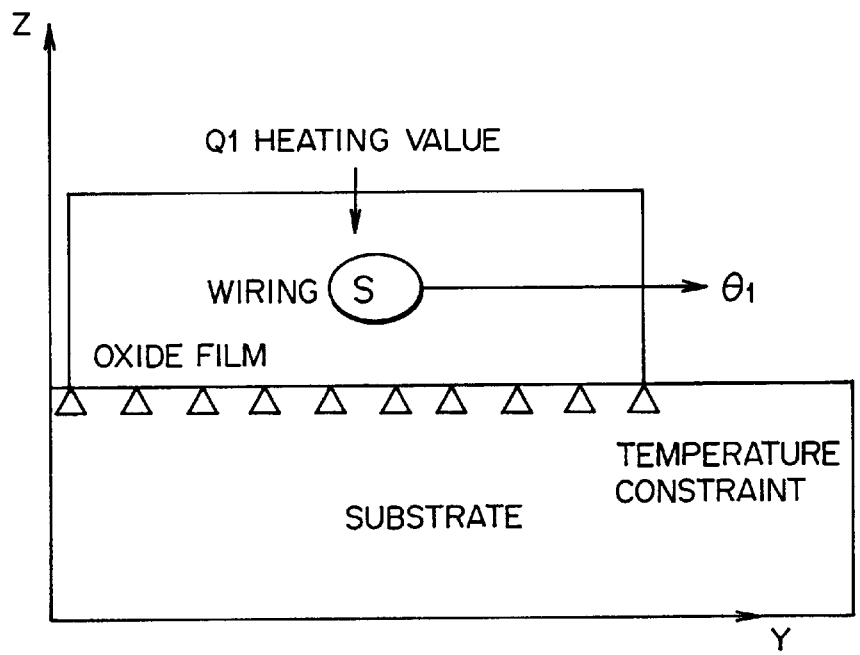
FIG. 5 is a cross-sectional view of the model of a wiring configuration in the embodiment according to the present invention.

The embodiments of the present invention will be specifically described with reference to the accompanying drawings. FIG. 4 is a flow chart showing a wiring temperature rise simulation method in one embodiment according to the present invention. FIG. 5 is a typical view showing the lateral cross-section of the wiring configuration. In this embodiment, an oxide film is provided on a silicon substrate and an aluminum wiring is provided on the oxide film. An interlayer insulating film (or oxide film) is further provided on the aluminum wiring. As shown in FIG. 5, a void occurs to a model configuration having a wiring layer embedded in the oxide film.

First, as shown in FIG. 5, a two-dimensional cross-sectional shape of the wiring is created (in step Q1). Thereafter, the cross-sectional area S of the wiring is obtained (in step Q2). Based on the above, various simulation conditions are estimated. The factor of determining accuracy in equation (2) shown in below is the accuracy of the cross-sectional area S and that of the heat capacity $C_1$. If there is an error in the cross-sectional area S in the order of $\Delta S$ in LSI manufacture, there is no point in obtaining the heat capacity $C_1$ with far higher accuracy than the error in the order of $\Delta S$. The cross-sectional shape of the wiring is divided into meshes so as to obtain the heat capacity $C_1$ with the same accuracy as that of the cross-sectional area S.

Next, two-dimensional thermal analysis simulation is conducted (in step Q3). As shown in FIG. 5, while a thermal quantity $Q_1$ is applied to every unit length of the cross-section of the wiring and a predetermined heat constraint is given to the surface of the substrate, two-dimensional thermal analysis simulation is conducted. Using this simulation for the cross-section of the wiring, a heat capacity $C_1=Q_1/\theta_1$ for every unit length of the wiring is obtained. The two-dimensional thermal analysis simulation methods include, for example, a finite element method, a boundary element method and a difference calculus method. According to the present invention, a simulation method is used to obtain a heat capacity $C_1$ and, therefore, any of the above-stated methods can be applied.

next, based on the heat capacity $C_1$, a temperature rise distribution in the vicinity of the void in the wiring is obtained from equation (2) shown below (in step Q4).

$$\theta_0 = (Q_0/2)(\lambda S C_1)^{-1/2} \quad (2)$$

In the equation (2), $\lambda$ is the heat conductivity of the wiring, S is the cross-sectional area of the wiring in which the void occurs and $Q_0$ is the heat quantity of the void in the wiring.

The equation (2) is introduced as follows. Normally, a metal material and an oxide film differ in heat conductivity by about tens times to 100 times. Due to this, a heat is conducted through the aluminum wiring in the wiring length direction, while a heat is conducted in the two-dimensional cross-section of the oxide film. An equation of heat conduction is solved using these properties. Namely, while a void is placed on an origin, the x axis is in the wiring length direction, an equation of $-q_1+q_2+q_3=0$ is solved, where a thermal quantity flowing from the wiring to a micro-segment dx of the wiring, i.e., $q_1=-\lambda S d\theta/dx$, a thermal quantity flowing through the wiring, i.e., $q_2=-\lambda S d(\theta+\Delta\theta)/dx$ and a thermal quantity flowing through the oxide film, i.e., $q_3=C_1\theta dx$. In this case, conditions that if $x=0$, $\theta=\theta_0$ and $q_1=Q_0/2$ and if $x=\infty$, $\theta=0$ are set as boundary conditions. As a result, $\theta_0$ is expressed by the mathematical expression (2) as shown above.

Figure 6:
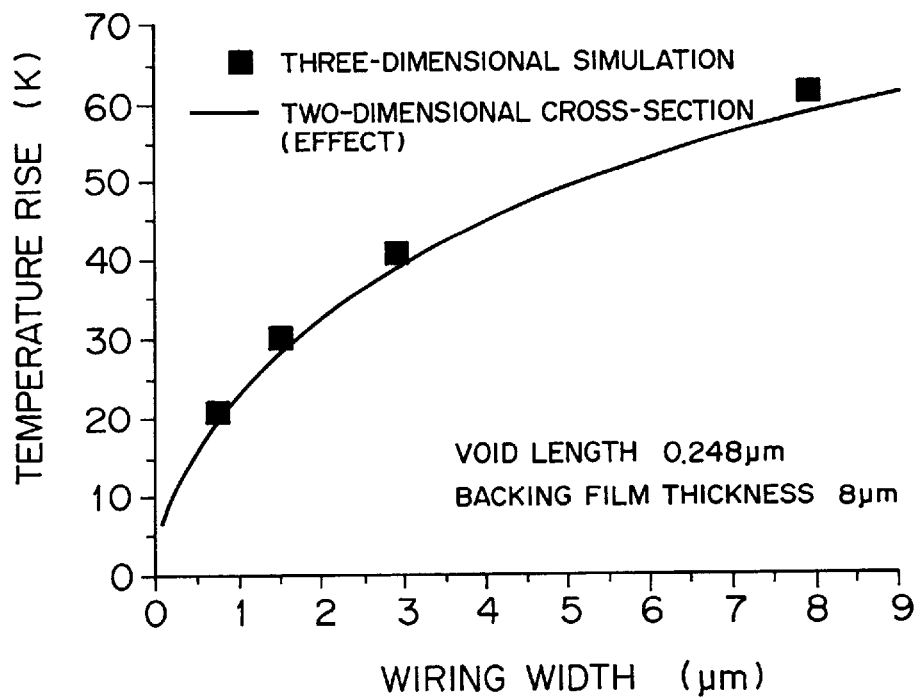
FIG. 6 is a graph showing the comparison of the result of temperature rise simulation in the embodiment according to the present invention with the conventional three-dimensional analysis.
Figure 7:
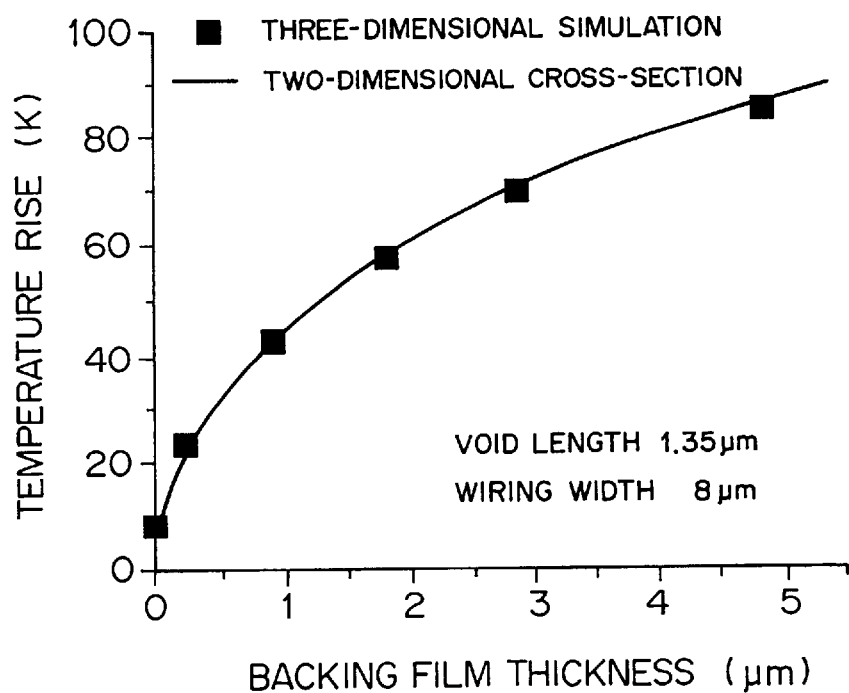
FIG. 7 is a graph showing the comparison of the result of the temperature rise simulation in the embodiment according to the present invention with the conventional three-dimensional analysis.

The relationship between the rise $\theta_0$ in the temperature of the wiring in the vicinity of the void thus obtained by the simulation method and the wiring width is shown in the graph of FIG. 6 (dependency of the temperature rise $\theta_0$ on the wiring width). The relationship between the temperature rise $\theta_0$ of the wiring in the vicinity of the void and the thickness of a backing film (which is between the wiring and the substrate) is shown in the graph of FIG. 7 (dependency of the temperature rise $\theta_0$ on the backing film thickness). In FIGS. 6 and 7, data indicated by ■ is temperature rise obtained by the conventional three-dimensional thermal analysis simulation. As shown in FIGS. 6 and 7, an estimate of temperature rise obtained by the two-dimensional thermal analysis simulation and the one-dimensional approximate equation (equation (2)) is quite similar to that obtained by the conventional method. It is understood, therefore, that temperature rise can be estimated with high accuracy in this embodiment. The temperature rise of the wiring in the vicinity of the void can be obtained with an accuracy of 6% or less in comparison with the conventional three-dimensional simulation method. The aluminum wiring has a heat conductivity of about 170 times as high as that of the oxide film. Theoretically, an error resulting from a physical numeric value of a temperature rise by a combination of two materials which greatly differ in heat conductivity, is 1% or less. This follows that an error of 6% stated above is mainly due to simulation analysis and does not have any influence in practice.

In this embodiment, to conduct simulation to the cross section of a two-dimensional configuration, the input of an analysis model configuration is simplified, time for creating a mesh on a computer is made shorter then in the conventional method by about $1/15$, analysis and calculation time is made shorter by about $1/20$ and the capacity of a memory and that of a disk required for analysis can be saved to about $1/20$.

Figure 8:
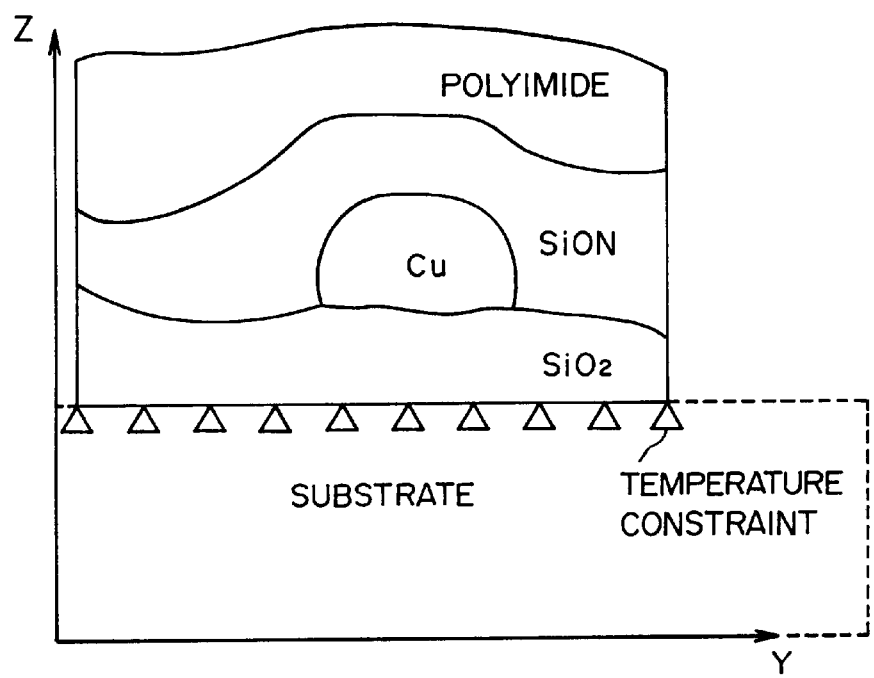
FIG. 8 shows another wiring model in the embodiment according to the present invention.

It is noted that the present invention is applicable not only to a relatively simple wiring configuration shown in FIG. 5, but also to a complicated wiring configuration as shown in FIG. 8. In FIG. 8, an $SiO_2$ layer is provided on a substrate, a Cu wiring is provided on the $SiO_2$ layer, an SiON interlayer insulating film is provided on the Cu wiring and a polyimide layer is further provided on the SiON interlayer insulating film. It is possible to estimate the temperature rise of the wiring in the vicinity of a void with high accuracy from the model of FIG. 8 by means of two-dimensional thermal analysis simulation and a one-dimensional approximate expression.

A wiring material is not limited to aluminum or copper. Various metal materials, such as tungsten, can be used for the wiring material to conduct highly accurate simulation. As an insulating film, a polyimide film, an SiON film or a zircon film which is sufficiently lower in heat conductivity than the metal material may be used instead of the oxide film. In practice, even if tungsten, which has the lowest heat conductivity, is selected as a wiring material from among the above-mentioned wiring materials and zircon, which has the highest heat conductivity, is selected as an insulating film material from among the above-mentioned insulating materials, the error resulting from the physical numeric value of temperature rise by this combination is as small as about 3%. The error is sufficiently smaller than that in the simulation analysis.

Figure 9:
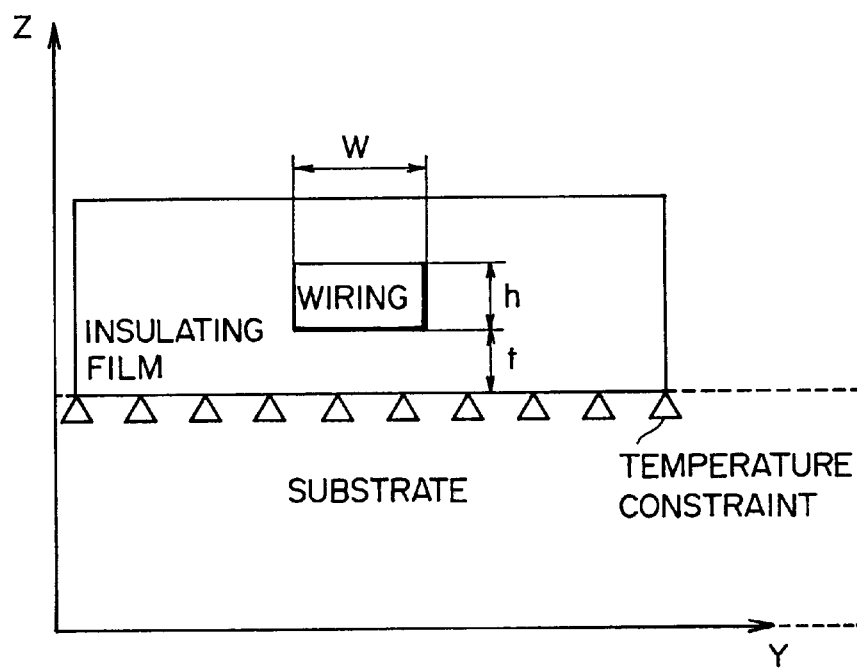
FIG. 9 is a cross-sectional view showing a wiring configuration in another embodiment method according to the present invention.

Next, a second embodiment according to the present invention will be described with reference to FIG. 9. In this embodiment, dependencies of a heat capacity $C_1$ for every unit length of a wiring on wiring width, wiring thickness and backing film thickness are known in advance. FIG. 9 illustrates a model in this embodiment, where the cross-section of the wiring is rectangular, wiring width is W, wiring thickness is h and the thickness of the backing film is t. The electric capacity of the wiring, in the conditions that wiring width is W, wiring thickness is h and the thickness of the backing film is t, is disclosed by a reference "T. Sakurai and K. Tamura, IEEE Trans. Electron Devices, vol. ED-30, NO. 2, p. 183, February 1983". In the above-stated model, both the electric capacity and the heat capacity are expressed by the Laplace equation.

Consequently, if the electric charges are made correspondent to thermal quantity and electric potential is to temperature rise, the equation for the electric capacity and that for the heat capacity are equal to each other. Taking this into consideration, if $\lambda'$ is given as the heat conductivity of the backing film, $C_1$ is expressed by the following equation (3).

$$C_1=\lambda'\{(W/t)+(2.80/1.15)\,(h/t)^{0.222}\} \quad (3)$$

In this embodiment, therefore, the steps $Q_1$, $Q_2$ and $Q_3$ shown in FIG. 4 can be omitted. This allows further shortening calculation time in this embodiment.

In the model shown in FIG. 8, C1 can obtained with an accuracy of 6% or less if $0.3<W/t<30$, $0.3<h/t<30$. The error in such a range fall within a range required for analysis and has no adverse effect on the analysis in practice.

What is claimed is:

1. A computer implemented wiring temperature rise simulation method comprising the steps of:

obtaining a heat capacity $C_1$ from an equation of $C_1=\lambda'\{((W/t)+(2.80/1.15)\,(h/t)^{0.222}\}$, where W is a wiring width, h is a wiring thickness, t is a substrate film thickness and $\lambda'$ is a heat conductivity of the substrate film; and obtaining a wiring temperature rise $\theta_0$ based on one-dimensional approximate expression of $\theta_0=(Q_0/2)(\lambda^*SC_1)^{-1/2}$ along a wiring length direction, where $\theta_0$ is a wiring temperature rise at a portion of the wiring in which a void occurs, $Q_0$ is a heat quantity of the void in the wiring, $\lambda$ is a heat conductivity of the wiring and S is a cross-sectional area of the wiring.

* * * * *